United States Patent [19]

Hrouda

[11] Patent Number: 4,487,204

[45] Date of Patent: Dec. 11, 1984

[54] DEVICE FOR APPLYING HAEMOSTATIC CLIPS

[75] Inventor: Georges Hrouda, Paris, France

[73] Assignee: Nomel, France

[21] Appl. No.: 433,672

[22] Filed: Oct. 12, 1982

[30] Foreign Application Priority Data

Oct. 14, 1981 [FR] France ................................ 81 19348
Feb. 12, 1982 [FR] France ................................ 82 02366

[51] Int. Cl.³ ............................................. A61B 17/12
[52] U.S. Cl. ................................... 128/325; 128/321;
 128/326; 227/DIG. 1; 29/243.56; 72/410
[58] Field of Search .............. 128/325, 326, 321, 346,
 128/330, 316; 29/243.56; 72/410; 227/DIG. 1;
 81/9.3, 303–312; 119/135; 40/301, 302, 304

[56] References Cited

U.S. PATENT DOCUMENTS

| 979,609 | 12/1910 | Vaughn | 81/303 X |
| 2,347,300 | 4/1944 | Thierwechter | 81/303 |
| 2,635,238 | 4/1953 | Garland | 227/DIG. 1 X |
| 2,972,791 | 2/1961 | Kelem | 29/243.56 |
| 3,015,824 | 1/1962 | Richardson | 72/410 X |
| 3,126,772 | 3/1964 | Haucke | 81/310 X |
| 3,780,416 | 12/1973 | Rider | 128/346 X |

FOREIGN PATENT DOCUMENTS

| 2462646 | 3/1981 | France | 128/346 |
| 2069848 | 9/1981 | United Kingdom | 128/326 |

Primary Examiner—Michael H. Thaler
Attorney, Agent, or Firm—Steinberg & Raskin

[57] ABSTRACT

A device for applying haemostatic clips for closing a duct having a flexible wall located between two legs of one haemostatic clip. This device, of a type exhibiting the shape of forceps, comprises two pivotally interconnected arms operating two jaws between which the clip is interposed. One of these jaws comprises two jaw elements arranged to be successively applied onto the other of these jaws, a first jaw element arranged to form the haemostatic clip into a loop with the ends thereof in overlapping relationship, and a second jaw element for flattening the thus-formed loop until the flexible duct is fully obturated.

23 Claims, 14 Drawing Figures

DEVICE FOR APPLYING HAEMOSTATIC CLIPS

BACKGROUND OF THE INVENTION

The present invention relates to a device for applying haemostatic clips for closing a duct having a flexible wall onto such a duct and haemostatic forceps or clips.

It is more particularly directed to a device for applying haemostatic clips for effecting a quick ligature of blood vessels as required in surgery upon the ablation or removal of an organ for instance, such an appliance device being readily usable by and reliable or dependable for the surgeon.

The use of haemostatic clips for clamping and shutting off blood vessels during a surgical operation is well known in practice and many haemostatic clip applying devices and haemostatic clips have made the subject matter of numerous prior patents of invention.

With the known haemostatic clips applying devices it is merely possible to bring the legs of the haemostatic clips together, such a bringing together being restrained by the size of the vessel to close or the thickness of the flesh sticking to the wall of this vessel. It is thus impossible with the known applying device to positively and reliably or safely lock the ends or noses of the haemostatic clips in order to avoid the opening of said clips during the surgical operation.

SUMMARY OF THE INVENTION

The object of the present invention is to obviate all of these inconveniences by providing a clip applying device enabling the surgeon to take from a clip distributor device or from a support or holder device the clips one by one by merely positioning the applying device within said distributor and to apply the haemostatic clip thus taken therefrom about a vessel thereby performing a reliable closing of said vessel together with a positive locking of the end noses of the haemostatic clip.

For that purpose, the object of the invention is the provision of a device for applying haemostatic clips consisting in withdrawing a haemostatic clips or clip for instance from a haemostatic clips distributor device, accommodating a yielding or flexible duct to be closed or shut off such as a blood vessel between both legs of the haemostatic clips thus taken therefrom and closing or shutting off said duct by closing said forceps.

According to the invention, the closing of said clip is carried out by successively bringing the ends of the clip together to form a loop, overlapping said ends to lock said clip and eventually crushing the loop thus formed until obturation of the flexible duct.

Said applying device being shaped as a forceps comprising two pivotally interconnected arms actuating two jaws, said arms comprising at their free ends generally ring-like gripping means adapted to the shapes of the fingers of one hand.

According to the invention, this device is characterized in that one of the jaws comprises two elements, one element arranged to form a loop together with a covering or a lap of the ends of the haemostatic clip and a second element for crushing the loop thus formed until a full obturation of the flexible duct or blood vessel is achieved.

According to a first embodiment of the invention, the first aforesaid element is connected to a resiliently deformable member, said member being pivotally connected to both aforesaid arms of the applying device, the pivoting and deformation of said member being controlled by these two arms. The second element is located within a central opening of said first element, said second element being at least temporarily connected to one of the arms of the device. According to a preferred embodiment of the invention, the second element is made in one piece or integral with one arm of the clip applying device.

Advantageously, at least one of the jaws comprises on its inner surface a longitudinal groove forming a receiving means for the haemostatic clip allowing a proper positioning of the latter between both jaws of the clip applying device.

In the first preferred embodiment of the invention, in particular for applying haemostatic clip comprising one leg with a curved or bent end or nose, the jaw onto which are applied both aforesaid elements comprises one curved or bent end forming a means for receiving said clip to hold and guide at least one part of said curved or bent end of the haemostatic clip whereas the end of the first element comprises a deforming element adapted to act upon said curved end of the clip upon a closing motion of the jaws to perform the covering or overlapping of both ends of the haemostatic clip and the positive locking thereof.

This deforming element advantageously comprises at its inner surface a groove the bottom of which defines a concave curve for guiding and bending the curved end of the haemostatic clip over the end of the other leg of said clip, whereas the walls of the groove form guide surfaces to avoid any sidewise shift of said haemostatic clip.

According to a second embodiment of the invention, the first arm of the haemostatic clip applying device comprises a first arm element connected to said first jaw element and a second arm element connected to said second jaw element.

Thus, with this device, the surgeon forms a loop locked about the flexible duct by drawing the second arm and the first arm element together and then, by operating the second arm element, the surgeon deforms the loop thus provided by moving the second jaw element towards the second jaw by applying a force corresponding substantially to the resistance of the blodd vessel to be obturated to deformation.

This device advantageously comprises a biassing or return spring element arranged between the first and second aforesaid arm elements for keeping the second jaw element in a position spaced from the second jaw when the device is in open position.

Moreover, it is also possible to provide a finger-like element projecting sidewise from said second jaw element and extending into a notch provided on the first aforesaid jaw element for limiting the motion of said second jaw element when the device is in open position.

According to still another characterizing feature of the second embodiment of the invention, the end of the first aforesaid arm element comprises a ring-like gripping means having a shape advantageously adapted to or mating the shape of the corresponding finger of the practitioner and the end of the second arm element is merely curved outwards of said device for merely preventing the finger from sliding out of the clip applying device.

Thus, this device may be easily handled by the surgeon who has two fingers only arranged in the gripping rings of the device, the third finger having to operate the second arm element while merely bearing thereon.

The applying devices according to the invention make it therefore possible on the one hand to reliably take a haemostatic clip from a distribution device and on the other hand to apply this clip upon a flexible duct such as a blood vessel, to carry out a positive locking of said haemostatic clip irrespective of the size of the vessel or of the body of flesh adhering thereto, and eventually to close the haemostatic clip for obturating or shutting off the vessel, said closing being directly controlled by the action of the clip upon the vessel.

Furthermore, both embodiments of a haemostatic clip applying device according to the invention, which comprise each one a haemostatic clip centering groove provided on the inside face of each jaw, advantageously comprise at least within the centering groove of said second jaw, at least one teat projecting into said groove and cooperating with a recess of the haemostatic clip.

The central portion of the end of the second jaw is advantageously curved towards the first jaw to form a haemostatic clip receiving means and for allowing the haemostatic clip to be inserted without any interference with said teat.

Moreover, said first jaw element comprises one end forming a nose directed towards said second jaw and comprising at its outermost edge a central groove for receiving or accommodating the curved end of said second jaw and at its inner edge two side teats co-operating with side recesses of the haemostatic clip.

According to still a further characterizing feature, said nose-shaped end of the first jaw element as well as said teats are removably secured onto said applying device for instance through screwing, riveting or like means.

BRIEF DESCRIPTION OF THE DRAWINGS

For a full understanding of the invention, reference is made to the following description, taken in connection with the accompanying drawings, in which.

DETAILED DESCRIPTION OF PREFERRED EMBODIMENTS

Advantageously, each haemostatic clip 2 consists of a flexible strip or blade exhibiting substantially at its central portion a beginning bend 2a so as to define two legs forming therebetween a substantially open angle with two free end portions 2c,2b. One of these end portions, for instance 2b, is curved or bent either into a loop or into a hook as shown in FIGS. 1 and 5 to 7.

A first preferred embodiment of the haemostatic clip applying device 20 will be described with reference to FIGS. 1 to 7. The haemostatic clip applying device 20 is of the forceps shaped kind comprising two arms 21,22 mounted in pivoting relationship with respect to each other about a pivot pin 23 for moving jaws 24,25 between which is arranged a haemostatic clip 2 in particular by means of a haemostatic clip distributing or carrying device. The arms 21,22 exhibit at their free ends, ring-like gripping means 26 for enabling the surgeon's fingers to be inserted therein. Both arms 21,22 are kept in spaced or spread-apart position by a spring 27 secured with one of its ends to one of the arms 22 and bearing with its other end upon the other arm 21. The opening of the arms and accordingly of the jaws is limited by stops 28. In the preferred embodiment of the invention and as shown on FIGS. 5 to 6, these stops 28 are constituted by shoulders provided on the arms 22, 21 at their pivotal connection about the pivot pin 23. It should be understood that other embodiments of these stops may be carried out without leaving the scope of the invention.

Figures 1, 2, 3, 4:
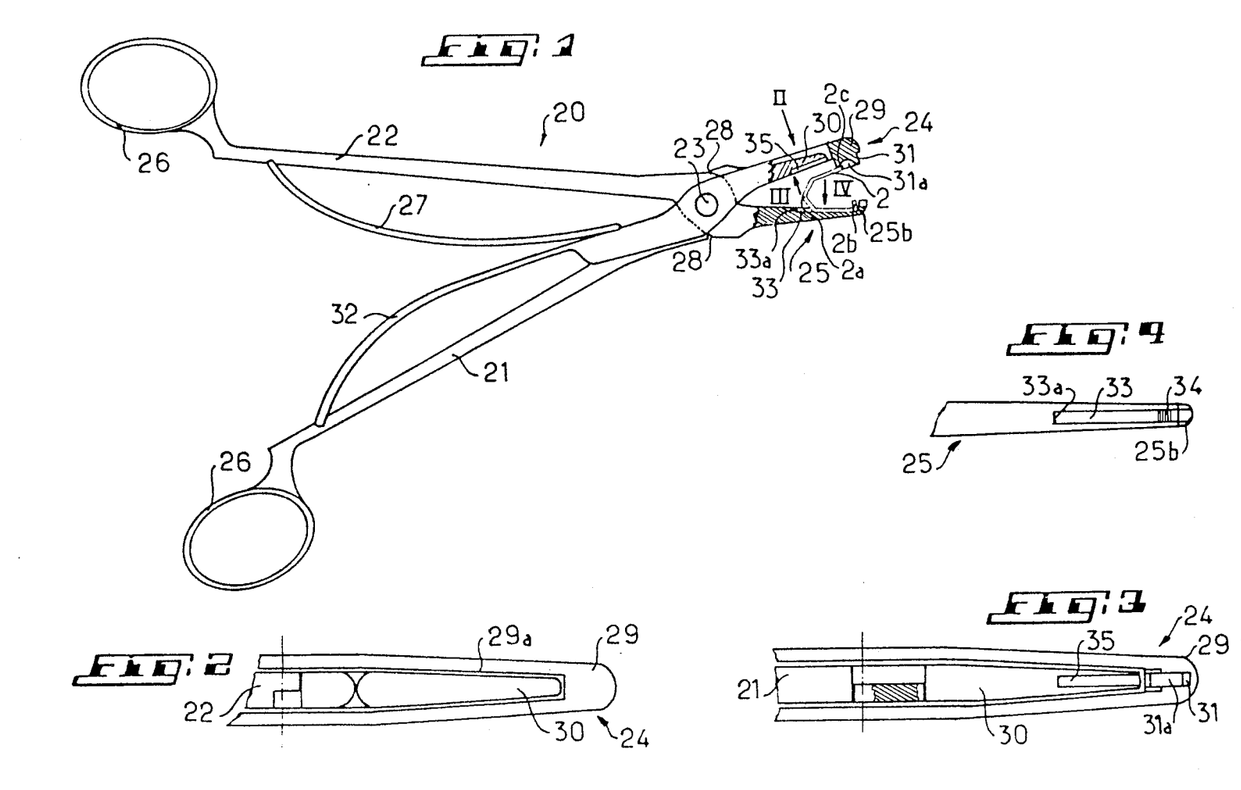
FIG. 1 is a diagrammatic view with parts broken away showing a first embodiment of the clip applying device according to the invention, in which a haemostatic clip is positioned prior to its application.
FIG. 2 is a top view seen in the direction of the arrow II of FIG. 1.
FIG. 3 is a view seen in the direction of the arrow III of FIG. 1 and illustrating the inner surface of one jaw of the applying device according to the invention.
FIG. 4 is a view seen in the direction of the arrow IV of FIG. 1 and showing the inner surface of the other jaw of the applying device according to the invention.

According to the invention, the clip applying device 20 comprises a jaw 24 including two jaw elements 29,30 arranged for being successively applied upon the other jaw 25.

In this first embodiment shown, the first jaw element 29 comprises at its end an element 31 projecting towards the other jaw 25 and made preferably in one piece or integral with said jaw element 29 and formed with a groove 31a at its inner surface.

This first jaw element 29 is advantageously connected to a deformable arm 32 pivotally mounted about the pin 23 and the end of which bears upon one of the arms 21 for instance.

Moreover, this jaw element 29 defines a central opening 29a in which is accommodated the second jaw element 30 which is connected to the arm 21. In the preferred embodiment of the invention, the arm 21 and the second jaw element 30 form together one single part or unit pivotally mounted about the pivot pin 23.

Referring to FIG. 4, the second jaw 25 exhibits, on its inner face, a longitudinal groove 33 forming a means for receiving the haemostatic clip 2. Moreover, when the haemostatic clip 2 used exhibits a leg with a curved or bent end 2b, the jaw 25 has a curved or bent end 25b to form a receiving means and for guiding and maintaining at least one part of the bent end 2b of the haemostatic clip 2.

The groove 33 may advantageously comprise at least one preferably saw-tooth like crosswise projection 34 co-operating for instance with cross-wise projections provided on the outer surface adjacent to the ends of the legs of the haemostatic clip 2.

Moreover, the longitudinal groove 33 ends with a shoulder 33a forming a stop for keeping the haemostatic clip 2 in proper position in particular during the closing of the jaws 24,25. This stop 33a may also be constituted by an element having for instance resilient properties and projecting from the surface of the jaw 25, the jaw element 30 then comprising a recess for receiving said stop in the closed position of the jaws 24,25.

Furthermore, as shown on FIG. 3, the second element also comprises a longitudinal groove 35 allowing the haemostatic clip 2 to be kept in proper position upon the closing of the jaws 24 and 25.

Figure 5:
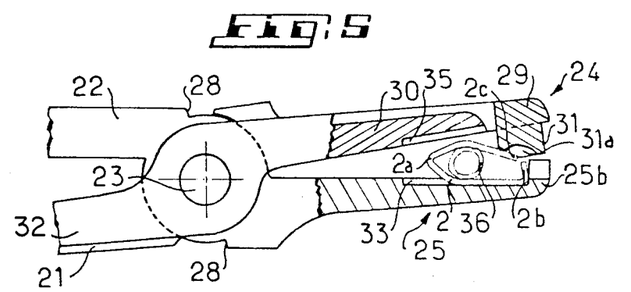
FIGS. 5 to 7 are enlarged views of the end of the clip applying device according to a first embodiment of the invention, illustrating various positions of the jaws and jaw elements upon the application of a haemostatic forceps onto a flexible duct.

With more particular reference to FIGS. 5 to 7, the operation of the first embodiment of the applying device 20 of the present invention will be described.

After a haemostatic clip 2 has been taken for instance by inserting the ends of the jaws 24,25 into a haemostatic clip distribution or carrying device, the haemostatic clip 2 is arranged between the jaws of the clip applying device 20 in the position shown on FIG. 1. Thus, one leg of the haemostatic clip 2 is in engagement with the jaw 25, the end of the other leg engaging the deforming element 31 i.e. the end of the first jaw element 29.

However, without leaving the scope of the invention, it is of course possible that the second jaw element 30 be in engagement with one leg of the haemostatic forceps 2 so as to thereby provide an improved hold of the haemostatic clip 2.

Figure 6:
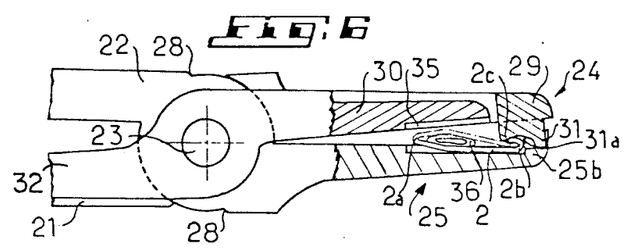

The surgeon then positions through the agency of the arms 22, 21 the haemostatic clip 2 about one flexible duct such as a blood vessel 36 and then by bringing both arms 22, 21 together i.e. against the force of the spring 27, the surgeon applies the first jaw element 29 upon the jaw 25 and thus brings the ends of both legs of the haemostatic clip 2 together to form a closed loop as shown on FIG. 6. During this bringing together the curved or bent end 2b of the clip engages the bottom of the groove 31a which has a concave curved shape for folding back the end 2b over the other straight end of the haemostatic clip 2.

Thus, in the position shown on FIG. 6, the haemostatic clip 2 has its ends positively locked but the blood vessel 36 is not obturated.

Then, by obturation of the arms 21, 22 against the force of the spring 32 of the deforming arm connected to the first jaw element 29, the second jaw element 30 is applied upon the jaw 25 for crushing the loop formed and thereby obturating the blood vessel 36. This crushing of the haemostatic clip 2 however, is limited only by the thickness of the wall of the blood vessel 36 and therefore the surgeon may effectively control the obturation of this vessel.

Figure 7:
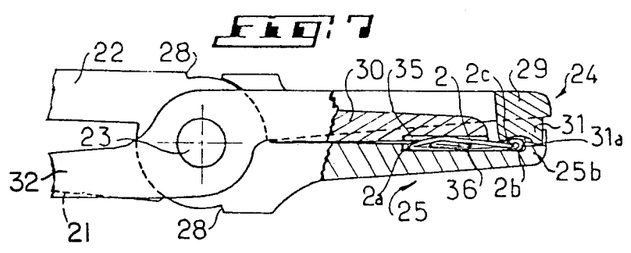

As shown on FIG. 7, it is clearly seen that, upon crushing the haemostatic clip 2, the straight leg slides within the curved or bent end of the other leg, thereby improving the locking of the haemostatic clip.

Accordingly, the first embodiment of the haemostatic clip applying device 20 of the invention, makes it possible in a first step to perform a positive locking of the haemostatic clip through overlapping or straddling of its two ends while forming a closed loop. It is easily understandable that such a locking is carried out irrespective of the size of the blood vessel 36 or of the body of flesh which is adhering to its wall. Then the surgeon may, by operating the arms 21,22 of the clip applying device 20, crush or flatten the loop for obturating the vessel 36, this obturation being solely controlled by the resistance of the vessel 36 to flattening or crushing.

A second embodiment of the haemostatic clip applying device according to the invention will now be described with reference to FIGS. 8 to 14.

Figure 8:
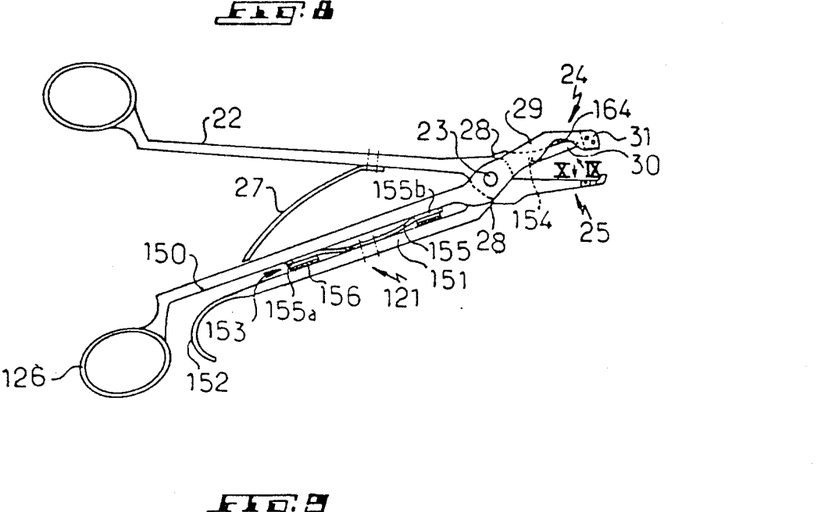
FIG. 8 is a diagrammatic view illustrating a second embodiment of the clip applying device of the invention shown in open position.

Referring to FIG. 8, the haemostatic clip applying device is of the forceps type comprising two arms 22,121 mounted in pivoting relationship with respect to each other about a pivot pin 23 for displacing the jaws 24,25 between which is arranged a haemostatic clip 2. This haemostatic forceps is for instance arranged between both the jaws 24 and 25 by means of a clip distribution device.

Both arms, 22,121 are kept in spaced or spread-apart position by a spring 27 secured with one of its ends to one of the arms 22 and bearing with its other end onto the other arm 121.

Moreover, the opening of the arms and accordingly of the jaws, is restrained by stops 28. The jaw 24 comprises two jaw elements 29,30 arranged for being successively applied upon the other jaw 25. The first jaw element 29 comprises at its end an element 31 projecting towards the other jaw 25 thereby defining a nose and exhibits a central opening 29a in which is housed the second jaw element 30. Furthermore, the nose 31 is formed at its inner surface with a groove 31a, the bottom of which has a shape allowing the end of a haemostatic clip to be curved or bent inwards and to be closed as clearly shown on FIGS. 11 to 13 and previously described.

Figure 9:
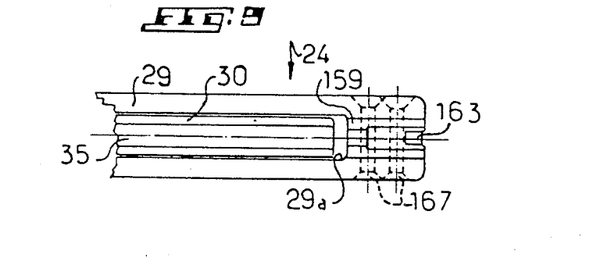
FIG. 9 is a view seen in the direction of the arrow IX of FIG. 8 and showing the inner surface of one jaw of the second embodiment of the applying device.
Figure 10:
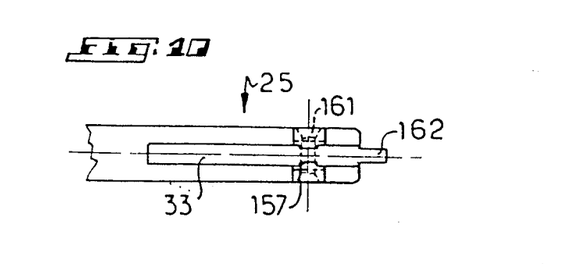
FIG. 10 is a view seen in the direction of the arrow X of FIG. 8 and showing the inner surface of the other jaw of this second embodiment of the applying device.

Moreover, the inner surfaces of the second jaw 25 and of the second jaw element 30 comprise a central groove 33,35, respectively, for the centering of the haemostatic clip 2.

All of these arrangements have already been described for the first embodiment of the haemostatic clip applying device.

In this second embodiment, the arm 121 of the applying device comprises a first arm element 150 including at its end a ring-shaped gripping means 126 and connected to the first jaw element 29 of the first jaw 24.

Advantageously, the first jaw element 29 and the arm element 150 are made in one piece or integral with each other the whole unit being mounted for swinging motion about the pin 23.

In addition, the arm 121 comprises a second arm element 151 connected to the second jaw element 30 and also mounted for rotation about the pin 23. This second arm element 151 advantageously has one end 152 thereof curved or bent inwards and is slightly spaced from the arm 150 in the open position of the applying device.

The jaw element 30 and the arm 151 are advantageously made in one piece.

Figure 11:
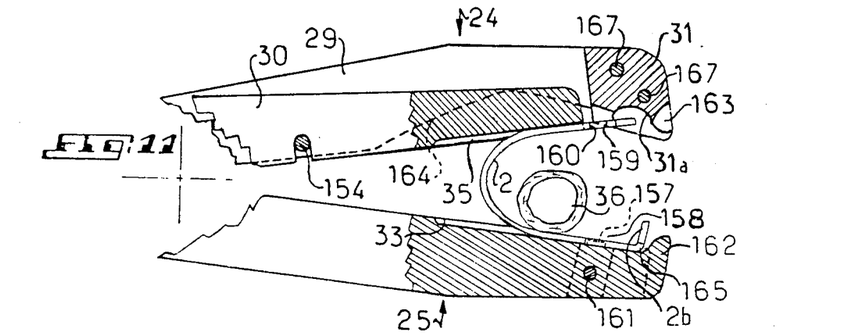
FIGS. 11 to 13 are views drawn on an enlarged scale and showing the ends of the jaws of the clip applying device of FIG. 8, illustrating the various positions of the jaws and jaw elements upon the application of a haemostatic clip onto a flexible duct.
Figure 12:
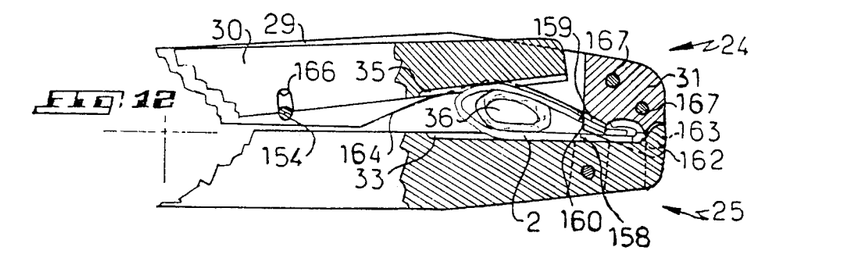
Figure 13:
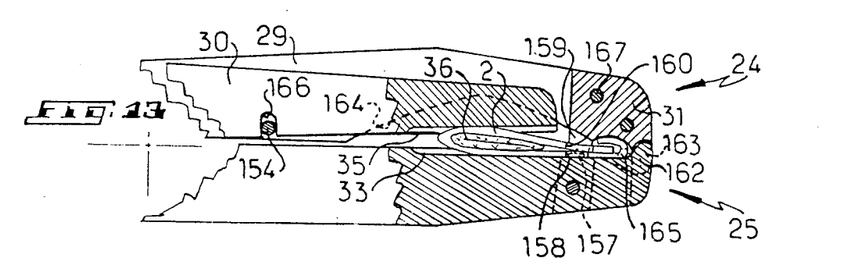

Moreover, in order to prevent the arm element 151 from moving away from the arm element 150 when the applying device is in open position, and accordingly to limit the opening of the jaw element 30, there is provided a stoplike element which for instance is either a biassing or return spring element 153 arranged between both legs or a finger 154 secured sidewise onto the jaw 30 and engaging a notch 166 in the jaw 29 as clearly shown on FIGS. 11 to 13. It is also possible to provide an applying device comprising these two appliances 153,154.

In the second embodiment shown, the return spring element 153 consists of a spring leaf, blade or plate 155 fastened with its central portion to the arm element 151 and the ends 155a,155b of which are slidably fitted into housings 155 provided on the arm element 150. The biassing or restoring force of the spring 155 should be relatively weak and advantageously smaller than the force required to deform the haemostatic clip 2 and substantially lower than the resistance strength to deformation of the flexible duct or blood vessel 36.

Furthermore, at least one teat 157 or like formation and preferably two teats are mounted in opposite or confronting relationship in the jaw 25 on either side of the central groove 33. These teats are engaging side recesses 158 formed in the haemostatic clip 2 to constitute an abutment for stopping and holding the haemostatic clip against motion during its application upon a flexible duct. In this second preferred embodiment of the invention there are also provided two substantially like teats 159 on the inner edge of the nose 31 of the first jaw element 29 which are engaging, mating or complementary side recesses 160 of the haemostatic clip 2.

Preferably, these teats 157,159 are removably mounted on the jaw 25 or the nose 31 through screwing or riveting means diagrammatically shown at 161.

The teat or teats 157 may of course be provided in the central part of the groove 33 to co-operate with a recess 160 mating with or complementary to the haemostatic clip without leaving the scope of the invention.

Advantageously, to make possible an easy insertion of the forceps 2 between the jaws 25,24 of the applying device without interference with the teats 159,157, the central portion 162 only of the end of the jaw 25 is curved, bent or turned upwards to form a means for receiving the haemostatic clip and for keeping same in elevated position with respect to the teats 157 upon the insertion of the clip 2 into the applying device.

To allow the application of the jaw element 29 upon the jaw 25, the outer edge of the nose 31 exhibits a central groove 163 having a shape mating with or complementary to the curved or bent central portion 162 of the jaw 25.

The width of this central groove 163 is smaller than the width of the leg of the haemostatic clip 2 for keeping the latter in elevated position with respect to the teats 159 during the insertion of the clip 2 into the applying device and to advantageously cause the clip 2 to be symmetrically deformed or distorted.

Advantageously, the nose 31 is removably mounted upon the jaw element 29 to thereby allow its replacement when it is worn out, for instance by means of rivets 167.

At last, the jaw element 29 comprises directly upstream of the nose 31 a recess 164 for the passing of the flexible duct 36.

Referring more particularly to FIGS. 11 to 14, the operation of the second embodiment of the applying device will be described.

After a haemostatic clip 2 has been taken for instance through insertion of the ends of the jaws 24,25 into the housing of a haemostatic clip distributing device, the haemostatic clip 2 is arranged between the jaws of the clip applying device, the teats 157,159 engaging the mating or complementary recesses 158,160, respectively.

Thus, the haemostatic clip 2 is centered and kept in longitudinal position within the applying device.

Moreover, the second jaw element 30 is generally in engagement with one leg of the haemostatic clip 2 to thereby still further improve its hold.

The surgeon then positions through the agency of the arms 22 and 150 the haemostatic clip 2 about a flexible duct such as a blood vessel 36 and then by bringing both arms 22,150 together i.e. against the force of the spring 27, the surgeon applies the first jaw element 29 onto the jaw 25 and thereby causes the ends of both legs of the haemostatic clip 2 to be brought together to form a closed loop as shown on FIG. 12. During this bringing together, the curved or bent end 2b of the clip engages the bottom of the groove 31a of the nose 31 which has a concave curved shape for bending or folding back the end 2b over the other straight end of the haemostatic clip 2.

Thus, in the position shown on FIGS. 12, 13, the haemostatic clip 2 has its ends positively locked but the blood vessel 36 is not obturated.

Figure 14:
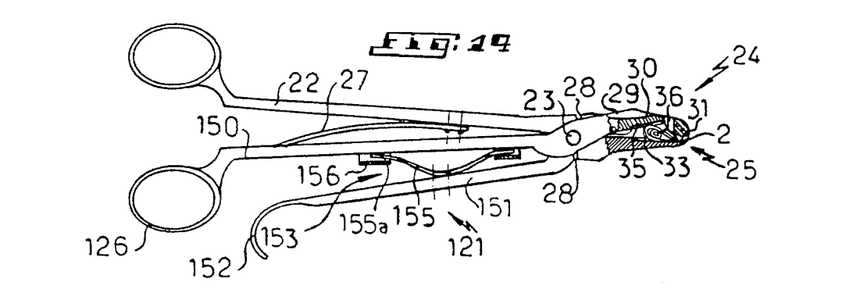
FIG. 14 is a diagrammatic view with parts broken away of a second embodiment of the applying device illustrating that position of the device which corresponds to the position of the jaws of FIG. 12.

As shown on FIG. 14, in this position the arms 22 and 150 are in a position close to each other to close the clip consisting of the jaw 25 and of the first jaw element 29, the arm element 151 being in a more or less spaced or spread-apart position with respect to the arm element 150. Thereby to obturate the blood vessel through flattening or crushing of the loop of the haemostatic clip 2 and therefore to close the jaw element 30 upon the jaw 25, it suffices to cause the second arm element 151 to be brought near or close to the arm element 150. This motion towards each other is performed by exerting a force adapted to overcome substantially solely the strength of the resistance of the blood vessel 36 to flattening or crushing, the strength of resistance to deformation or distortion of the clip 2 being weak in comparison with that of the blood vessel.

Therefore, this applying device enables the surgeon to control the force exerted for obturating a blood vessel against the strength or resistance of this vessel to flattening or crushing.

Once the clamping has been effected, by releasing the forces, the spring 27 will cause the applying device to open.

The present invention thus provides a haemostatic clip applying device for obturating a blood vessel by exerting a force corresponding substantially to the strength or resistance to flattening or crushing of the vessel. Moreover, the haemostatic clip is kept in position between both jaws on the one hand by central grooves and on the other hand by stop or abutment teats allowing to avoid longitudinal rearward or forward displacements of the jaws upon crushing of this clip. These teats may of course also be provided in both embodiments of the haemostatic clip applying device.

Moreover, for making possible an easy bending or curving of the curved end of the haemostatic clip 2 and an easier locking of this clip, side recesses 165 are provided at the curvature of the end 2b of the haemostatic clip 2.

It is of course possible without leaving the scope of the invention, to provide different embodiments for the opening limiting stops 28, 154,153 and in particular stops with adjustable positions.

It should be understood that the invention is not at all limited to the embodiments of the haemostatic clip applying device described and shown which have been given by way of example only. Thus, the jaw elements 29,30 constituting the jaw 24 of the applying device 20 may be made fast with the arms 21 and 22 of the device for pivoting therewith by any equivalent technical means such as a stop, cam or the like. The shapes of the ends of the jaws 24,25 are adapted or mating with the contour of the haemostatic clip used.

What is claimed is:

1. A haemostatic clip applying device on a flexible duct to be obturated, such as a blood vessel, said device exhibiting the shape of forceps and comprising two arms mounted in pivotal relationship with respect to one another about a pivot pin and having ring-like gripping means at free ends thereof for moving a pair of jaws between which a haemostatic clip is arranged, the haemostatic clip constituted by a flexible blade having two free end portions, one of which is bent into a hook, and two legs defined by a bend at a substantially central portion of the haemostatic clip to form therebetween a substantially open angle in which the flexible duct is situated, pivoting movement of said arms with said gripping means causing said jaws to bring both legs of the haemostatic clip together and lock the same to form a loop, followed by flattening of the loop or crushing of the legs of the haemostatic clip when one of said jaws is applied against the other of said jaws to obturate the flexible duct therebetween, wherein said jaw to be applied upon the other of said jaws comprises two jaw elements arranged to be successively applied onto the other of said jaws, a first one of said jaw elements pivotally connected to said first arm about said pin and having at an end thereof, an element projecting towards the other of said jaws and defining a substantially central opening, and a second jaw element accommodated within said substantially central opening of said first jaw element and also pivotally connected to said first arm, so that by bringing said first and second arms together, said first jaw element is applied upon the other of said jaws so that said projecting element folds the hooked end of the haemostatic clip back over the other, substantially straight end of the haemostatic clip to positively lock these ends, and by continuing to bring both said first and second arms together, said second jaw element is applied upon the other of said jaws for flattening or crushing the formed loop of the haemostatic clip, while effectively controlling the obturation of the flexible duct, with the haemostatic clip having a substantially straight operative position.

2. A device according to claim 1, wherein said first jaw element is connected to the end of a resiliently deformable member pivotally mounted about said pin, with the other end of said resiliently deformable member bearing upon said first arm, and said second jaw element is connected to said first arm.

3. A device according to claim 1, wherein said second jaw element is formed integrally with said first arm.

4. A device according to claim 1, wherein said projecting element comprises a groove along an inner surface thereof, the bottom of said groove defining a concave curve for guiding and bending the bent end of the haemostatic clip over the other, substantially straight end of the haemostatic clip.

5. A device according to claim 4, wherein said projecting element is formed integrally with said first jaw element.

6. A device according to claim 5, wherein the other of said two jaws comprises a bent end forming means for receiving the haemostatic clip, for retaining the same, and for guiding at least one portion of the bent end of the haemostatic clip.

7. A device according to claim 1, wherein the other of said two jaws and said second jaw element comprise a longitudinal groove along inner surfaces thereof, constituting means for receiving the haemostatic clip and for maintaining the same in a correct position during closure motion of said jaws.

8. A device according to claim 7, comprising at least one crosswise, saw-toothlike projection disposed in at least one of said longitudinal grooves along the inner surfaces of the other of said two jaws and said second jaw element.

9. A device according to claim 7, comprising at least one stop disposed in at least one of the longitudinal grooves along the inner surfaces of the other of said two jaws and said second jaw element, said stop spaced from the first one of said two jaws.

10. A device according to claim 1, wherein said first arm comprises a first arm element pivotally mounted about said pin and connected to said first jaw element, and a second arm element pivotally mounted about said pin and connected to said second jaw element.

11. A device according to claim 10, comprising a return spring element disposed between said first and second arm elements for keeping said second jaw element open when said device is in an open position.

12. A device according to claim 10, wherein said ring-like gripping means of said first arm is mounted on an end of said first arm element, and an end of said second arm element is bent outwardly from said device.

13. A device according to claim 10, additionally comprising at least one stop element for limiting opening of said second jaw element with respect to said first jaw element.

14. A device according to claim 13, wherein said at least one stop element comprises a finger projecting from one side face of one of said first or second jaw elements, and a notch in the other of said first or second jaw elements, with said finger engaging said notch.

15. A device according to claim 10, wherein a substantially central portion of an end of the other of said two jaws is bent towards the first one of said two jaws, to constitute means for receiving the haemostatic clip.

16. A device according to claim 15, wherein said projecting element of said first jaw element is in the shape of a nose and comprises a substantially central groove adapted to mate with said bent end of said other jaw, said substantially central groove in said projecting element having a width substantially narrower than a width of the haemostatic clip, and also comprising at least one side teat disposed on an inner edge of said projecting element, said teat adapted to engage a complementary side recess in the haemostatic clip.

17. A device according to claim 16, wherein said nose-shaped projecting element is removably secured onto said first jaw element.

18. A device according to claim 16, wherein said side teat is removably secured onto said first jaw element.

19. A device according to claim 7, comprising at least one projecting teat disposed on a portion of said longitudinal groove along the inner surface of the other of said two jaws, adapted to cooperate with at least one complementary recess in the haemostatic clip.

20. A device according to claim 19, wherein said projecting teat is removably secured onto the other of said two jaws.

21. A device according to claim 1, wherein recesses are provided at the curvature of the bent end of the haemostatic clip.

22. A haemostatic clip applying device on a flexible duct to be obturated, such as a blood vessel, said device exhibiting the shape of forceps and comprising first and second arms mounted in pivotal relationship with respect to one another about a pivot pin and having ring-like gripping means at free ends thereof for moving two jaws at the ends of said first and second arms opposite said gripping means, with a haemostatic clip disposed between said two jaws, the haemostatic clip constituted by a flexible blade having two free end portions, one of which is bent into a hook, and two legs defined by a bend in a substantially central portion of the haemostatic clip to form a substantially open angle therebetween, in which the flexible duct is disposed, pivoting movement of said first and second arms with said gripping means causing said two jaws to bring the two legs of the clip together and lock the same to form a loop, followed by flattening of the loop or crushing of the legs of the haemostatic clip when one of said two jaws is applied upon the other of said two jaws to obturate the flexible duct, wherein said jaw applied onto the other of said two jaws comprises two jaw elements arranged to be successively applied onto the other of said two jaws, a first jaw element connected to one end of a resiliently deformable member pivotally mounted about said pin, with the other end of said deformable member bearing upon a portion of said first arm, said first jaw element having at an end thereof, an element projecting toward the other of said two jaws and defining a substantially central opening therein, and a second jaw element accommodated within said substantially central opening of said first jaw element and connected to said first arm, so that, by bringing said first and second arms together, said first jaw element is applied upon the other of said two jaws so that said projecting element folds the hooked end of the haemostatic clip back over the other substantially straight end of the haemostatic clip to positively lock these ends, and by continuing to bring said first and second arms together, said second jaw element is applied upon the other of said two jaws for flattening or crushing the formed loop while effectively controlling the obturation of the flexible duct, with the clip having a substantially straight, operative position.

23. A haemostatic clip applying device on a flexible duct to be obturated, such as a blood vessel, said device exhibiting the shape of forceps and comprising, first and second arms mounted in pivotal relationship with respect to one another about a pivot pin, and having ring-like gripping means at free ends thereof for moving two jaws at opposite ends from said gripping means, with a haemostatic clip disposed between said two jaws, the haemostatic clip constituted by a flexible balde having two free end portions, one of which is bent into a hook, and two legs defined by a bend at a substantially central portion of the haemostatic clip, forming a substantially open angle therebetween, in which the flexible duct is disposed, pivoting movement of said arms with said gripping means causing said two jaws to bring the two legs of the haemostatic clip together and lock the same into a loop, followed by flattening of the loop or crushing of these legs when one of said jaws is applied upon the other of said two jaws to obturate the flexible duct, wherein said first arm comprises a first arm element pivotally mounted about said pin, and a second arm element pivotally mounted about said pin, and wherein said jaw applied onto the other of said two jaws comprises two jaw elements arranged to be successively applied onto the other of said two jaws, a first jaw element connected to said first arm element and having, at an end thereof, an element projecting towards the other of said two jaws and having a substantially central opening therein, a second jaw element accommodated within said substantially central opening of said first jaw element and connected to said second arm element, and a return spring element disposed between said first and second arm elements for keeping said second jaw element open when said device is in an open position, so that, by bringing said first and second arms together, said first jaw element is applied upon the other of said two jaws so that said projecting element folds the hooked end of the haemostatic clip back over the other, straight end of the haemostatic clip to positively lock these ends, and by continuing to bring said first and second arms together, said second jaw element is applied upon the other of said two jaws for flattening the formed loop or crushing the legs of the haemostatic clip, while effectively controlling the obturation of the flexible duct, with the clip having a substantially straight, operative position.

* * * * *